US00PP18120P2

(12) United States Plant Patent
Pierce

(10) Patent No.: US PP18,120 P2
(45) Date of Patent: Oct. 9, 2007

(54) ***ACHILLEA* PLANT NAMED 'GIPI WHIT'**

(50) Latin Name: *Achillea ptarmica L.*
Varietal Denomination: Gipi Whit

(75) Inventor: Robert Osteen Pierce, Watsonville, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/406,017

(22) Filed: Apr. 18, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—Jondle & Associates, P.C.

(57) ABSTRACT

An *achillea* plant particularly distinguished by numerous small, while, double flowers, medium green foliage with narrow leaves, a compact, low-spreading and mounding habit, vigorous with abundant branching, immature flowering stems that obscure the mature stems with spent flowers and good outdoor performance with good heat tolerance, is disclosed.

2 Drawing Sheets

Genus and species: *Achillea ptarmica* L.
Variety denomination: 'Gipi Whit'

BACKGROUND OF THE NEW PLANT

The present invention comprises a new and distinct cultivar of *achilea,* botanically known as *Achillea ptarmica* L. and hereinafter referred to by the cultivar name 'Gipi Whit'. Seed of the *achillea* variety 'The Pearl' (unpatented) which is an open-pollinated, seed propagated variety was sown in April 2003 and grown in Gilroy, Calif. in an evaluation field. A single plant selection was made in August 2003 from the resulting plants and asexually propagated.

The new cultivar was created in August 2003 in Gilroy, Calif. and has been asexually reproduced repeatedly by vegetative cuttings and tissue culture in Gilroy, Calif. and Moncarapacho, Portugal over a two-year period. The plant has also been trialed at Hillscheid, Germany. The present invention has been found to retain its distinctive characteristics through successive asexual propagations.

Plant Breeder's Rights for this cultivar have been applied for in Canada on Oct. 17, 2005 and with the European Union on Oct. 14, 2005.

SUMMARY OF THE INVENTION

The following are the most outstanding and distinguishing characteristics of the new cultivar when grown under normal horticultural practices in Hillscheid, Germany.

1. Numerous small, white, double flowers;
2. Medium green foliage with narrow leaves;
3. A compact, low-spreading and mounding habit;
4. Vigorous with abundant branching;
5. Immature flowering stems that obscure the mature stems with spent flowers; and
6. Good outdoor performance with good heat tolerance.

DESCRIPTION OF THE PHOTOGRAPHS

This new *achillea* plant is illustrated by the accompanying photographs which show overall plant habit including blooms, buds and foliage of the plant; the colors shown are as true as can be reasonably obtained by conventional photographic procedures. The photos are of plants grown in a greenhouse in Hillscheid, Germany in a Spring trial setting.

DESCRIPTION OF THE NEW CULTIVAR

Figure 1:
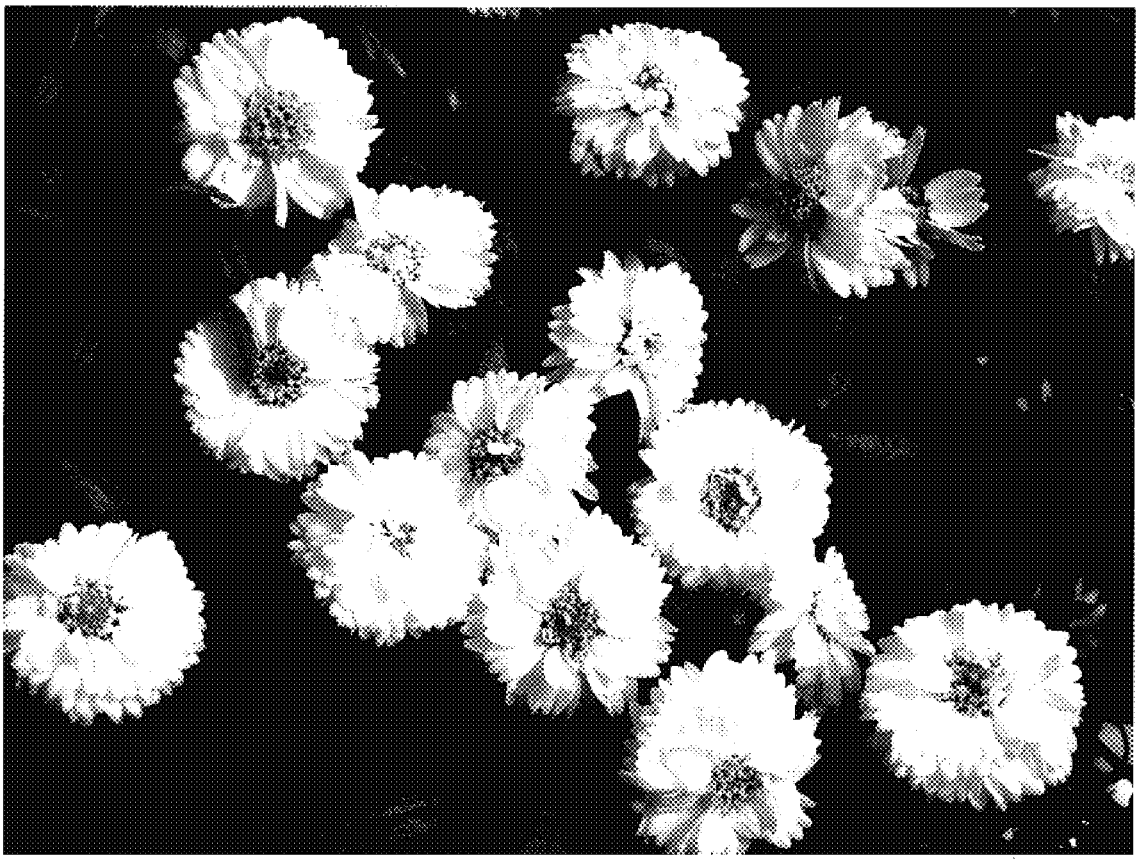
FIG. 1 shows a close-up of a portion of the plant including blooms and foliage of a 16-week-old plant.
Figure 2:
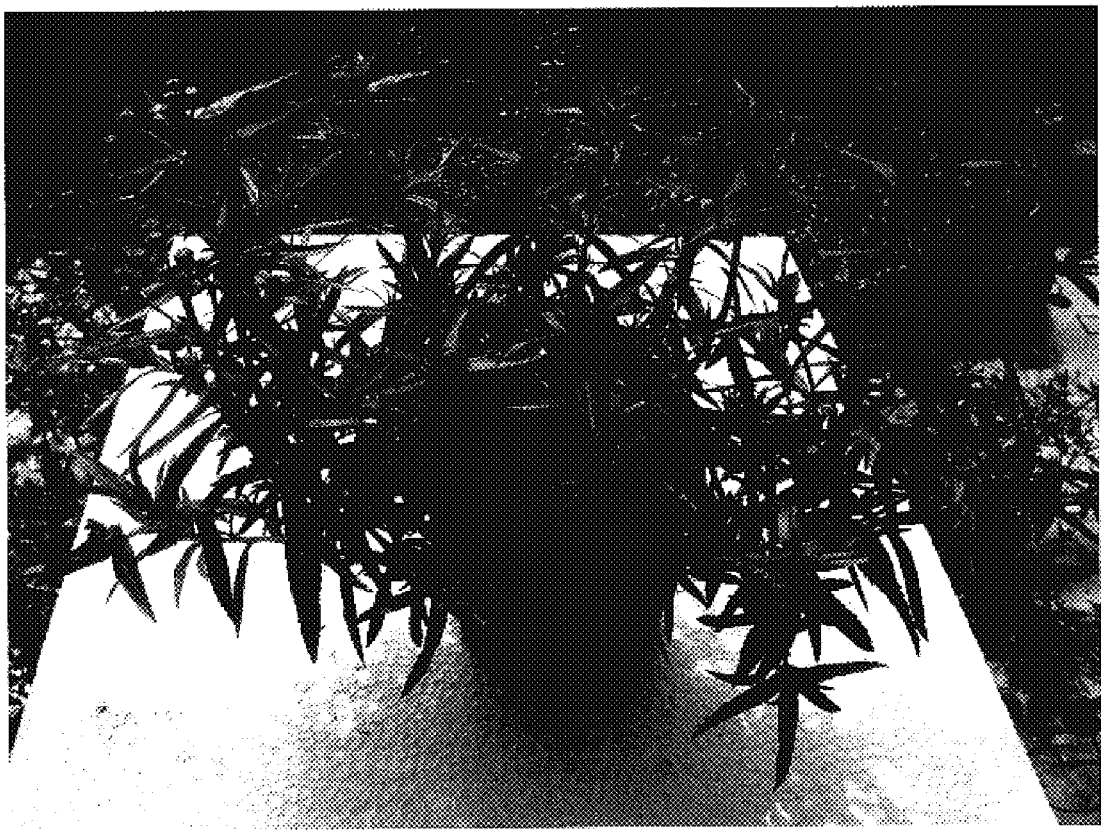
FIG. 2 shows the overall plant habit, including buds and foliage of a 10-week-old plant.

The following detailed descriptions set forth the distinctive characteristics of 'Gipi Whit'. The data which define these characteristics were collected from asexual reproductions carried out in Hillscheid, Germany. The plant history was taken on 7- to 8-week-old plants, pinched once, and grown in 12-cm pots in a greenhouse in Hillscheid, Germany in July and August 2005. Observations were made in mid-May 2005. Color readings were taken in the greenhouse in mid-May 2005 under natural light. Color references are primarily to the R.H.S. Colour Chart of The Royal Horticultural Society of London (RHS) (2001 edition).

DETAILED BOTANICAL DESCRIPTION

Classification:
*Family.*—Asteraceae.
*Botanical.*—*Achillea ptarmica* L.
*Common name.*—Sneezeweed or sneezewort.

Parentage:
*Parent.*—'The Pearl', a white-flowered, seed-propagated, open-pollinated variety (unpatented).

Growth:
*Form and habit.*—Spreading to decumbent; the immature flowering stems obscure the mature stems with spent flowers, thus reducing the time needed to remove any visible spent flowers.

*Growth and branching habit.*—Compact and free-branching Height (measured from the top of the soil): 15 cm to 21 cm.

*Width* (*horizontal plant diameter*).—35 cm to 40 cm.

*Time to produce a finished flowering plant.*—12 weeks for a 12-cm pot in the Spring.

*Outdoor plant performance.*—Use in mixed container plantings and as bedding plants.

*Time to initiate and develop roots.*—21 to 24 days.

*Root description.*—Fibrous, freely branching.

Stems:

*Number of branches per plant.*—35 to 50.

*Length* (*of basal branches*)—22 cm to 27 cm.

*Diameter* (*measured from the midpoint*).—0.3 cm.

*Internode length.*—1.5 cm to 2.5 cm.

*Color.*—RHS 145A.

*Anthocyanin.*—Absent.

*Texture.*—Pubescent; soft hair on immature stems and sparse hair on mature stems.

Leaves:

*Arrangement.*—Simple and alternate; partly appearing as whorls.

*Immature leaf.*—Color: Upper surface: RHS 143A. Lower surface: RHS 143B.

*Mature leaf.*—Color: Upper surface: RHS 137B. Lower surface: Between RHS 137B and RHS 143B. Length: 2.8 cm to 3.5 cm. Width: 0.5 cm to 0.7 cm. Shape: Lanceolate. Apex: Acute. Base: Attenuate. Margin: Serrate. Texture: Upper surface is slightly glossy and sparsely pubescent (with no to sparse hair) and lower surface is pubescent.

*Petioles.*—None, leaves are sessile.

Flower buds:

*Shape.*—Round and somewhat flattened.

*Length.*—0.4 cm.

*Diameter* (*horizontal*).—0.6 cm.

*Color* (*at tight bud*).—RHS 145B.

Inflorescence:

*Type.*—A capitulum (composite-type); solitary inflorescences emerge from the leaf axils at the upper nodes.

*Blooming habit.*—Continuously flowers from the Spring through the Fall.

*Number of inflorescences per stem.*—10 to 12.

*Lastingness of the individual blooms on the plant.*—3-weeks or greater, depending on humidity, temperature and light.

*Fragrance.*—None.

*Horizontal diameter of inflorescence.*—1.8 cm.

*Vertical diameter of inflorescence.*—0.9 cm.

*Disc diameter.*—0.4 cm to 0.5 cm.

*Disc floret.*—Quantity (per inflorescence): 25 to 30. Shape: 5-lobed and narrow funnel-shaped. Tube color (closed): RHS 150D (greenish-yellow). Tube color (mature): RHS 4D (cream-yellow). Length: 0.3 cm. Diameter (at apex): 0.15 cm. Apex: Broadly acute. Apex color: RHS 2D (pale yellow). Base: Fused.

*Ray florets.*—Quantity (per Inflorescence): 50 to 70. Shape: Lanceolate. Color (immature and mature): Upper surface: Pure white, whiter than RHS 155D. Lower surface: RHS 155D (white). Length: 0.6 cm. Width: 0.2 cm. Apex: Broadly acute. Base: Fused. Margin: Entire. Texture: Smooth and papillose.

*Penduncle.*—Color: RHS 143C. Length: 2.0 cm to 5.0 cm. Diameter: 0.2 cm. Texture: Weakly pubescent.

Reproductive organs:

*Androecium.*—Location: Present on disc florets only. Stamen quantity: One per floret. Filament: Color: RHS 150D. Length: 0.2 cm. Diameter: 0.015 cm. Anther: Pollen color: RHS 9A. Pollen amount: Moderate.

*Gynoecium.*—Location: Present on ray florets only. Quantity: One per floret, 2-lobed. Pistil length: 0.2 cm to 0.3 cm. Stigma: Color: RHS 151B, translucent. Style: Length: About 0.4 cm. Diameter: About 0.025 cm. Color: RHS 151B translucent, but lighter.

Fruit/Seed set: None observed.

Disease and insect resistance: Has not been evaluated.

COMPARISON WITH PARENTAL AND COMMERCIAL CULTIVARS

'Gipi White' differs from the parent 'The Pearl' (unpatented), in that 'Gipi Whit' has a more free-branching, spreading and mounding plant habit, while 'The Pearl' has upright-directed stems with fewer branches, is taller and is more recommended for use as a cut flower than 'Gipi Whit'.

'Gipi Whit' differs from the commercial variety 'Ballerina' (unpatented), in that 'Gipi Whit' has a more free-branching and mounding plant habit than 'Ballerina'.

I claim:

1. A new and distinct cultivar of *achillea* plant as shown and described herein.

* * * * *